(12) United States Patent
Suzuki et al.

(10) Patent No.: US 7,344,522 B2
(45) Date of Patent: Mar. 18, 2008

(54) ABSORBENT RENDERED THREE-DIMENSIONAL IN CENTRAL REGION BY WATER ABSORPTION, AND ABSORPTIVE ARTICLE USING THE SAME

(75) Inventors: Migaku Suzuki, Tokyo (JP); Katsuhiko Sugiyama, Aichi (JP); Satomi Takematsu, Tokyo (JP); Kazuyo Mori, Tokushima (JP)

(73) Assignee: Japan Absorbent Technology Institute, Tokyo (JP)

( * ) Notice: Subject to any disclaimer, the term of this patent is extended or adjusted under 35 U.S.C. 154(b) by 0 days.

(21) Appl. No.: 10/488,368

(22) PCT Filed: Sep. 6, 2002

(86) PCT No.: PCT/JP02/09099

§ 371 (c)(1),
(2), (4) Date: Mar. 2, 2004

(87) PCT Pub. No.: WO03/022193

PCT Pub. Date: Mar. 20, 2003

(65) Prior Publication Data

US 2004/0243081 A1    Dec. 2, 2004

(30) Foreign Application Priority Data

Sep. 7, 2001    (JP)    ............... 2001-271832

(51) Int. Cl.
  *A61F 13/20*    (2006.01)
(52) U.S. Cl. ............ 604/385.01; 604/385.12; 604/385.201; 604/378; 53/559
(58) Field of Classification Search ........... 604/385.01, 604/385.12, 385.201, 378, 367; 53/559
See application file for complete search history.

(56) References Cited

U.S. PATENT DOCUMENTS

| | | | | |
|---|---|---|---|---|
| 4,532,173 A | * | 7/1985 | Suzuki et al. ............ | 428/218 |
| 4,670,011 A | * | 6/1987 | Mesek ................. | 604/378 |
| 4,880,419 A | * | 11/1989 | Ness .................. | 604/368 |
| 5,593,399 A | * | 1/1997 | Tanzer et al. ........... | 604/378 |
| 5,643,238 A | * | 7/1997 | Baker ................. | 604/368 |
| 5,925,026 A | * | 7/1999 | Arteman et al. ......... | 604/383 |
| 6,066,775 A | * | 5/2000 | Bachar ................ | 604/378 |
| 6,293,935 B1 | * | 9/2001 | Kimura et al. .......... | 604/387 |
| 6,316,688 B1 | * | 11/2001 | Hammons et al. ....... | 604/378 |
| 6,326,525 B1 | * | 12/2001 | Hamajima et al. ....... | 604/378 |
| 6,610,038 B1 | * | 8/2003 | DiPalma et al. ...... | 604/385.12 |
| 6,700,034 B1 | * | 3/2004 | Lindsay et al. ......... | 604/378 |
| 6,730,068 B2 | * | 5/2004 | Kashiwagi et al. .... | 604/385.04 |
| 2001/0053901 A1 | * | 12/2001 | Mizutani et al. ........ | 604/381 |

FOREIGN PATENT DOCUMENTS

| | | | |
|---|---|---|---|
| EP | 1022003 A1 | * | 7/2000 |
| JP | 2-86521 | | 7/1990 |
| JP | 5-49658 A | | 3/1993 |
| JP | 9-313529 A | | 12/1997 |
| JP | 11-508482 | | 7/1999 |
| JP | 2000-51269 A | | 2/2000 |
| JP | 2000-201975 A | | 7/2000 |
| JP | 2001-212177 A | | 8/2001 |
| WO | WO 97/40803 | | 11/1997 |

* cited by examiner

*Primary Examiner*—Tatyana Zalukaeva
(74) *Attorney, Agent, or Firm*—Frommer Lawrence & Haug LLP; Ronald R. Santucci (57) ABSTRACT

An absorbent easily rendered three-dimensional in the central region by water absorption is composed of a sheet-like absorbent having regions where a highly absorptive component is present and regions where it is absent, these presence and absence regions parallelly extending lengthwise of a sheet-like base material and alternating with each other, the sheet-like base material being turned back along a bending line in the highly absorptive component absence regions of the sheet-like absorbent, there being at least one band-like portion of multilayer construction where the highly absorptive component presence regions are superposed in a plurality of layers.

12 Claims, 8 Drawing Sheets

ABSORBENT RENDERED THREE-DIMENSIONAL IN CENTRAL REGION BY WATER ABSORPTION, AND ABSORPTIVE ARTICLE USING THE SAME

This application is a 371 of PCT/JP02/09099 filed on Sep. 6, 2002, published on Mar. 20, 2003 under publication number WO 03/022193 A1 and claims priority benefits of Japanese Patent Application No. 2001-271832 filed Sep. 7, 2001.

TECHNICAL FIELD

The present invention relates to an absorbent that absorbs and holds there the fluid excretion from the human body and more particularly to an absorbent easily rendered three-dimensional by readily becoming filling out at the time of absorption to fit the three-dimensional contour of the human body. Furthermore, the present invention pertains to absorptive products equipped with the said absorbent, which is easily rendered three-dimensional in its central region by water absorption, as the absorbent element.

BACKGROUND ART

Traditionally, absorptive products comprising a liquid-permeable top sheet, a liquid-impermeable back sheet and the absorbent that intervenes between these sheets have been widely used for various purposes such as urine pads, incontinence products, diapers and the like. These absorptive products have tended to be thin in recent years, because the thickness of the absorbent has been reduced in order to eliminate stiffness and stickiness caused by the thickness of the absorbent.

A thin absorptive product allows a wearer to move easily, but at the same time it is prone to the problem of giving a feeling of discomfort to the wearer. This is due to its having an insufficient contact area with the discharging part of the wearer's body, resulting in the flowing of the liquid human waste along the wearer's body immediately after discharge. Also, thinness has been the cause of leakage when the product is used continuously over a long period of time.

In order to solve these problems, an attempt to improve close contact by adding a separately prepared bulky absorptive layer in the central region of the absorbent that constitutes the core is proposed. For example, in the PATENT ABSTRACTS OF JAPAN, Publication number: 2000-51269, an absorptive article which attempts to improve the fitting by laminating a narrow polymer sheet layer to the central part along the longitudinal direction of these pulp layers is disclosed.

A conventional technique such as the above, however, cannot eliminate the bulkiness of the absorbent because the voluminous flocculent pulp remains contained at a high content ratio in the absorbent layer which is the main absorbent component. Also, because its capability to retain absorbed fluid is insufficient, stickiness remains on the top sheet, resulting in giving an unpleasant feeling to the wearer in many cases.

Furthermore, because an absorbent sheet must be newly laminated in order to give a three-dimensional configuration to the center region, in addition to the increased cost of material, there is the problem of its leading to increased production costs.

DISCLOSURE OF INVENTION

An object of the present invention is to provide the absorbent and the absorptive article using this absorbent, the central portion of whose multilayer construction is formed without newly adding an absorbent sheet, but rather by using a simple and easy method, and whose ability to fit the discharging part of the human body is further improved by spontaneous bulging, while still being thin and compact before use.

In accordance with the present invention, an absorbent whose central area is easily rendered three-dimensional by water absorption is provided, where the absorbent is composed of an absorbent sheet having areas with super-adsorbent material and areas without super-absorbent materials, with these areas extending alternately in parallel lengthwise on a substrate sheet. At least one band-shaped portion of multilayer construction is formed by the said substrate sheet's being folded back along a folding line in the said areas without super-absorbent material of the said absorbent sheet, and the said areas with super-absorbent material being superposed in several layers. Herewith the surface of the said portion of multilayer construction and the surface of other portions are just about even when the said super absorbent component is in a dry state, but the said portion of multilayer construction bulges to a level higher than the other portions as liquid is absorbed.

Preferred forms of the above-described invention are given below.

The said portion of multilayer construction is present throughout the length of the absorbent sheet.

The said portion of multilayer construction has a length one half or less than one half of the entire length of the absorbent sheet and is present only in the center region in the longitudinal direction of the absorbent sheet.

In the areas without super-absorbent materials positioned on both sides, across the width, of the said portion of multilayer construction, slits extending in a longitudinal direction of the absorbent sheet are made, thus allowing the bulging, by absorbing liquid, of the said portion of multilayer construction, and with no widthwise binding effect from other portions.

In the center region of the said portion of multilayer construction, a central zone is formed by making two spaced slits extending in the direction perpendicular to the longitudinal direction of the absorbent sheet, thus allowing the easy bulging, by absorbing liquid, of the central zone of the said portion of multilayer construction, with no lengthwise binding effect from other portions.

By folding the two areas without super-absorbent material on both sides across the areas with super-absorbent material located in the center region of the absorbent sheet, to make a valley fold so that each folded portion faces the other, a three-layer section of multilayer construction of the areas with super-absorbent material is formed in the center region of the absorbent sheet.

The distance between the said valley folds opposite each other is retained at 5 mm or more, and the said portion of the multilayer construction bulges with two peaks when liquid is absorbed.

On both sides of the said portion of the multilayer construction formed in the center region widthwise of the absorbent sheet, with an appropriate space in between, are the side portions of the multilayer construction formed by folding the absorbent sheet; between the said center portion of the multilayer construction and each side portion of the multilayer construction, troughs to channel fluid are formed.

Further, band-shaped acquisition layers extending along both sides of the said side portions of the multilayer construction are provided.

On the undersurface of at least one portion of the multilayer construction of the said center portion and each side portion of the multilayer construction, band-shaped acquisition layers extending longitudinally along the said undersurface are further provided.

The said areas with super-absorbent material formed on the absorbent sheet is composed of the super absorbent layer with a super-absorptive resin content ratio of 50% or more and the said areas without super-absorbent material are made of the said substrate sheet only.

The areas with super-absorbent material and the areas without super-absorbent material of the absorbent sheet are distributed alternately in continuous narrow lines.

Also, according to the present invention, absorptive products equipped as their absorbent element with the said absorbent, which is easily rendered three-dimensional in the central region by water absorption, are provided.

BEST MODE FOR CARRYING OUT THE INVENTION

The absorbent easily rendered three-dimensional of the present invention will be explained in further detail with reference to the drawings.

Figure 1:
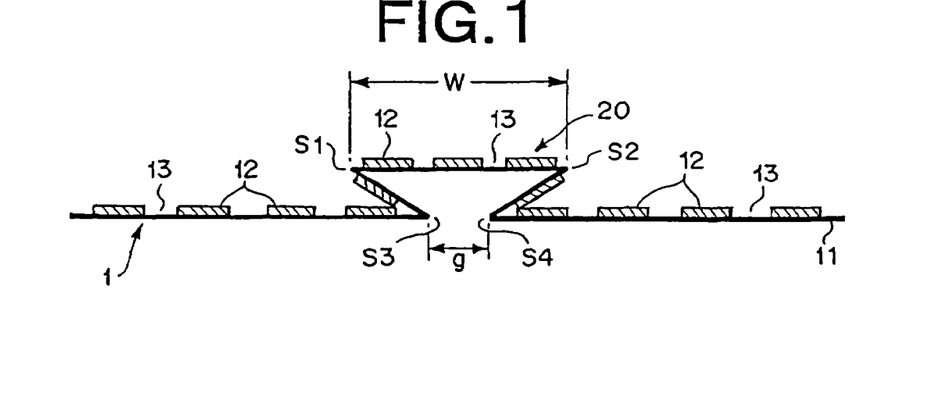
FIG. 1 is a widthwise sectional view of the absorbent which is easily rendered three-dimensional in the first example.

FIG. 1 explains the basic makeup of the absorbent easily rendered three-dimensional of the present invention and is a sectional view taken along the line perpendicular to the longitudinal direction. In this view, the absorbent sheet 1 comprises the band-shaped areas with super-absorbent material 12 and areas without super-absorbent material 13 alternately formed on the surface of a non-woven like liquid-permeable substrate sheet 11 and the portion of the multilayer construction 20 formed in the widthwise central region by folding the absorbent sheet 1 extends in the longitudinal direction of the absorbent sheet 1.

In addition, FIG. 1 demonstrates an example of a portion of the multilayer construction 20, as the absorbent easily rendered three-dimensional of the present invention, being formed to stand up from the surface on the side where super-absorbent material 12 of the absorbent sheet 1 is provided. A portion of the multilayer construction 20 may also be formed to stand up from the top surface while providing the super-absorbent material on the bottom surface side of the substrate sheet 11. Further, the absorbent sheet 1 may also be formed by positioning in parallel the super-absorbent material in a band shape at regular intervals between the substrate sheets and by bonding in between each band of super-absorbent material by such means as heat sealing.

Figure 2A:
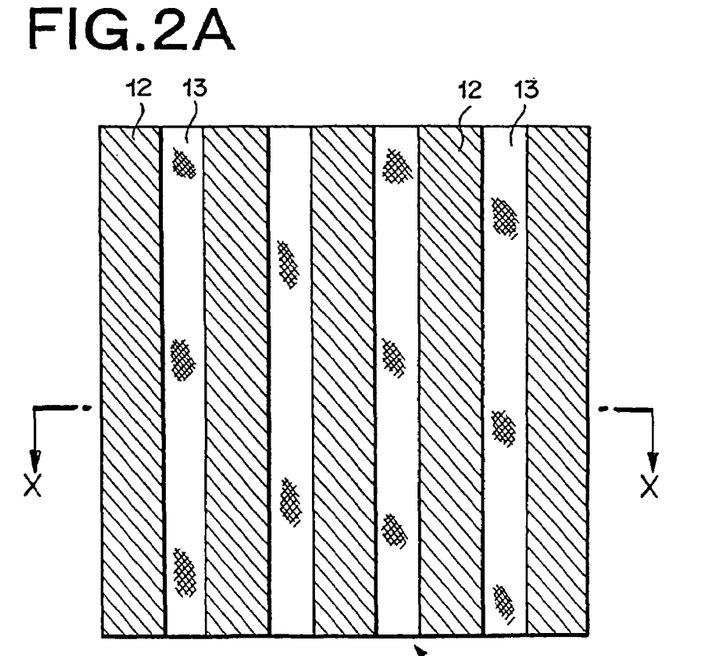
FIGS. 2A and 2B are a plan view and a sectional view of the absorbent sheet comprising the absorbent easily rendered three-dimensional, shown in FIG. 1.
Figure 2B:
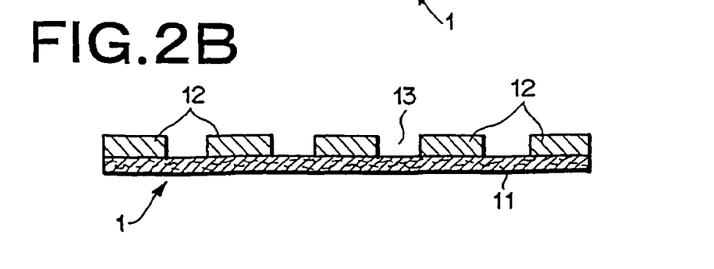

FIGS. 2A and 2B are a plan view and a sectional view of a portion of the absorbent sheet 1 used to construct the absorbent easily rendered three-dimensional shown in FIG. 1. This absorbent sheet 1 is formed by applying, using a line-coating technique, the super-absorbent material on the surface of the substrate sheet 11 made of non-woven fabric, preferably of bulky and air permeable, in a band shape in parallel with each other and extending along the longitudinal direction of the substrate sheet 11; the areas 12 composed of appropriately spaced multiple bands of super-absorbent material and the areas 13 where there are no super-absorbent material are positioned alternately.

The areas with super-absorbent material 12 are the main absorptive component of the absorbent easily rendered three-dimensional. Also, the areas without super-absorbent material 13 function as the dispersing/acquisition area, and are preferred to have a permeable construction through which air can travel freely, both before and after liquid absorption by the absorbent sheet 1.

The areas with super-absorbent material 12 provided on the absorbent sheet 1 preferably are made of super-absorptive resin and microfibrillated cellulose. More precisely, the region is formed by applying a coating material, made by dispersing super-absorptive resin and microfibrillated cellulose in a mixed solvent made of water and organic solvent such as propylene glycol and methanol, in bands on non-woven fabric made of fiber material generally used for non-woven fabrics and are of polyethylene, polypropylene, polyester, as well as those made of other thermoplastic resin, rayon, cotton and the like.

Microfibrillated cellulose is a microscopic fiber with an average fiber length of 0.1 mm or less which is obtained by defibrating of highly sheared wood pulp.

Because the absorbent sheet can be obtained by coating non-woven fabric with a super-absorbent material, line-coating at any desired width is possible. Application patterns can also be selected from the combination of full-surface coating and line-coating or line-coating only. The desirable mode of the absorbent sheet has a continuous phase of the areas with super-absorbent material and the areas without super-absorbent material contacting each other. Especially, if the areas without super-absorbent material are made of substrate sheet only, for example, the areas without super-absorbent material will be extremely soft compared to the areas with super-absorbent material, making easy folding possible and thus the areas with super-absorbent material can be folded together making them contact with each other.

Even if the areas with super-absorbent material are folded together to form stacked layers by folding at the areas without super-absorbent material, because the substrate sheet itself is extremely thin, there is little impact on the total thickness of the folded area. Also, because the main component of the areas with super-absorbent material is super-absorptive resin, compared to conventional pulp/super-absorbent mixtures, its thickness is only as little as ½ to ⅕, so even when these areas are folded as described above, the resultant convex portion is not highly visible, making possible the formation of the absorbent easily rendered three-dimensional which is compact and with overall thinness.

The areas without super-absorbent material, by positioning them widthwise in the center and lengthwise throughout the length of the absorbent, can be folded along the folding lines located within the areas without super-absorbent material and thereby create a continuous multilayer construction in longitudinal direction. Also, in case industrial production is carried out, continuous folding is readily made possible by a simple apparatus such as a guide plate.

With the absorbent easily rendered three-dimensional of the present invention, even if several areas without super-absorbent material are positioned on the absorbent sheet, not all of them always have to be folded. The areas with super-absorbent material can be positioned in the desired width and in desired number. Also, for the portion of the multilayer construction, its top layer may consist of super-absorbent material only, or areas without super-absorbent material may be mixed in.

Also, the absorbent easily rendered three-dimensional of the present invention may be constructed by folding a single sheet of absorbent sheet, or by using the multiple number of absorbent sheets stacked together. In case two or more of the absorbent sheets are combined, they may be folded together after stacking them together, or overlay the sheet in the bottom layer after folding the absorbent sheet.

Once again in FIG. 1, the portion of the multilayer construction 20 is formed by folding the absorbent sheet 1 along the folding lines S1 and S2 within the areas without super-absorbent material 13, spaced by any given width W and located on both sides of the widthwise center line of the absorbent sheet, making a mountain fold for each, and then folding again, this time making a valley fold for each, along the folding lines S3 and S4 within the areas without super-absorbent material 13 located outside the mountain folding lines S1 and S2.

As a result of these foldings, the folding lines S3 and S4 become opposing lines spaced by space g and the absorbent sheet 1 at the portion of multilayer construction 20 will be in a three-layer construction in most parts, except in space g, making this portion three times as thick as the rest.

By narrowing space g between the folding lines S3 and S4, the said three-layer construction will have almost uniform thickness, and in this case the portion of multilayer construction 20 will swell by absorbing liquid human waste, bulge uniformly overall, and improve close contact to the human body.

Also, when the width of space g is made 5 mm or more, the construction will be of one layer in the center and of three layers on both sides of it. In this case, after liquid absorption, the portion of multilayer construction 20 will bulge higher on the sides than in the center, forming a sectional configuration similar to the letter M. The concaved portion in the center thus becomes a channel for the fluid and dispersion of liquid is improved.

Figure 3A:
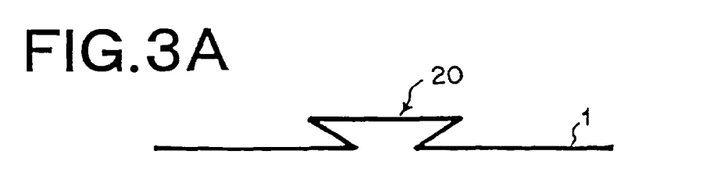
FIGS. 3A and 3B are illustrative sectional views of the states, before and after water absorption, of an example of a portion of the multilayer construction.
Figure 3B:
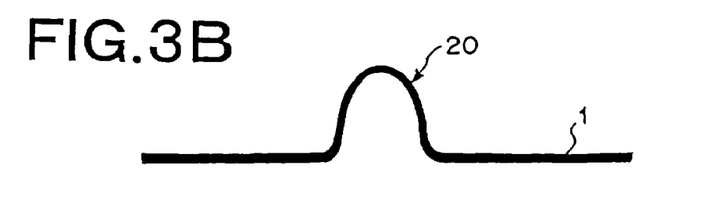

FIG. 3's illustrative views thus, show the absorbent easily rendered three-dimensional with a portion of multilayer construction 20 in the center widthwise, in the state before liquid absorption 3A and the swollen and expanded state after liquid absorption 3B. In FIGS. 3A and 3B, especially the portion of multilayer construction 20 in the central region will have an arch-like bulging, making this region three-dimensional and allowing it to closely fit the groove contour of the discharging part of the wearer's body. As a result, even when the wearer makes a bodily movement, there is no fear of dislodging, and the maximum absorption function will be displayed.

In the present invention, it is possible to form a region of multilayer construction in the center by folding as described above multiple times, and the more numerous the layers become, the more readily swelling and bulging by liquid absorption takes place, making it spontaneously reach the three-dimensional state. The absorbent in the construction that enables spontaneous bulging and then readily reaching the three-dimensional state as just described is referred to as "the absorbent easily rendered three-dimensional" in this Description.

The function of spontaneously becoming three-dimensional as described above becomes prominent when the direction in which it bulges is restricted, and furthermore that extent can be controlled.

Figure 4A:
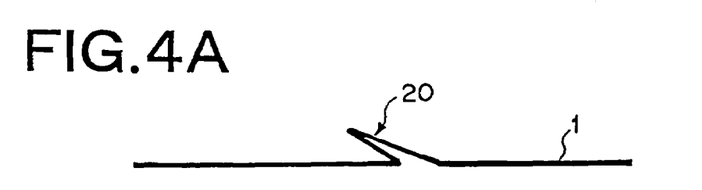
FIGS. 4A and 4B are illustrative sectional views of the states, before and after water absorption, of an example of a portion of the multilayer construction.
Figure 4B:
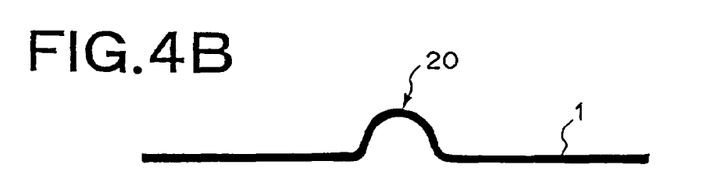
Figure 5A:
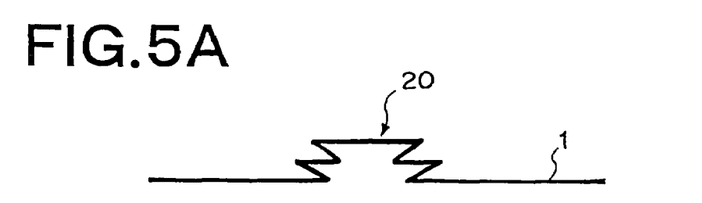
FIGS. 5A and 5B are illustrative sectional views of the states, before and after water absorption, of an example of a portion of the multilayer construction.
Figure 5B:
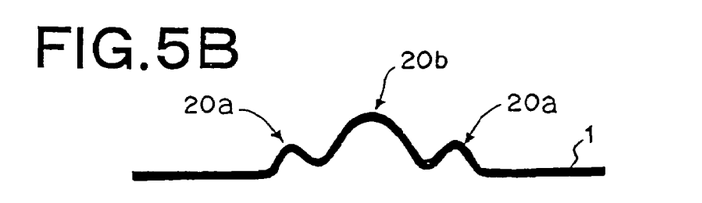

FIG. 3 through FIG. 5 are illustrative views of different configurations of the portion of multilayer construction 20, made by using the absorbent sheet 1 with the areas with super-absorbent material and the areas without super-absorbent material alternately formed in a band shape parallel to each other along the longitudinal direction of the non-elongation substrate sheet, changing the positions and the spacing width of the folding lines. In each of these Figures respectively, A demonstrates the state before absorbing, and B the state after liquid absorption and the resultant overall thickness increase caused by swelling and expansion.

Figure 6A:
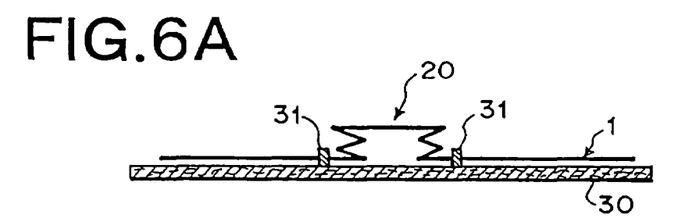
FIGS. 6A and 6B are illustrative sectional views of the states, before and after water absorption, of the portion of the multilayer construction of the absorbent easily rendered three-dimensional in the second example.
Figure 6B:
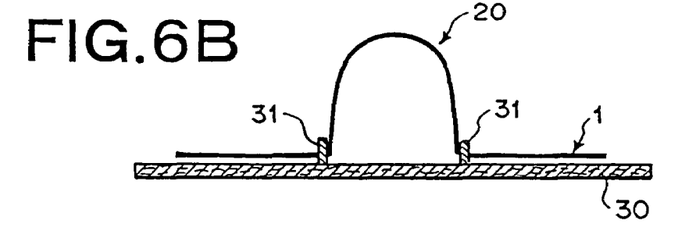

Views in FIG. 6 exhibit the other modes of examples of the absorbent easily rendered three-dimensional of the present invention. This absorbent easily rendered three-dimensional uses the non-elongation material sheet 30 including non-woven fabrics such as SB, SMS, films such as PE and PP, or their laminated structure, and on top it the absorbent sheet 1 with a portion of multilayer construction 20 is superimposed, and then at both sides of the portion of multilayer construction 20, it is fixed by means of hot melt 31 to the non-elongation material sheet 30.

In this case, because the elongation of the absorbent sheet 1 in the widthwise direction of the portion of multilayer construction 20 is restricted due to having been fixed in place by hot melt, the possible direction of bulging by absorption of the portion of multilayer construction 20 will only be upward, quickly achieving an extremely stable three-dimensional state.

Furthermore, with the absorbent easily rendered three-dimensional of the present invention, in addition to the portion of the multilayer construction in the widthwise central region of the absorbent sheet, on both sides of it the side portions of the multilayer construction may be provided.

Figure 7:
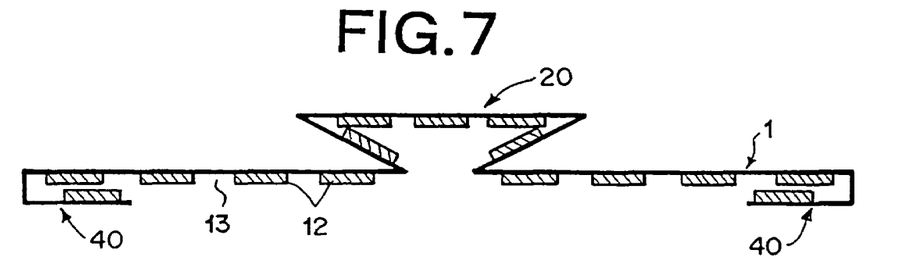
FIG. 7 is an illustrative sectional view of the portion of the multilayer construction of the absorbent easily rendered three-dimensional in the third example.

One such example is shown in FIG. 7. In the widthwise central region of the absorbent sheet 1 comprising the absorbent easily rendered three-dimensional in this example, while having the surface with super-absorbent component disposed facing downward, the central portion of the multilayer construction 20, the same as the absorbent easily rendered three-dimensional shown in FIG. 1, is formed facing upward, and at the same time, on both sides of it, the side portions of the multilayer construction 40, made with a portion of the side edges of the absorbent sheet 1 folded double in the direction opposite of the central portion of the multilayer construction 20 (or the reverse side when the absorbent easily rendered three-dimensional is in use) is formed.

Figure 8:
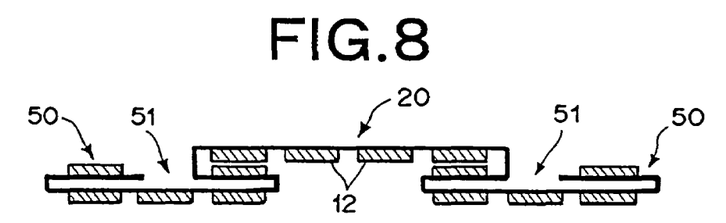
FIG. 8 is an illustrative sectional view of the portion of the multilayer construction of the absorbent easily rendered three-dimensional in the fourth example.

FIG. 8 shows an example of forming the side edge portions of the multilayer construction 50 by folding the absorbent sheet 1 on the very surface on which the portion of the multilayer construction 20 is formed. In the absorbent easily rendered three-dimensional of this example, the channel 51 with its opening on the surface side will be formed between the central portion of the multilayer construction 20 and each side portion of the multilayer construction 50. This channel 51 directs the fluid that was not absorbed in the portion of the multilayer construction 20 into channel 51, and quickly has the fluid absorbed and held by the areas with super-absorbent material within channel 51.

Figure 9:
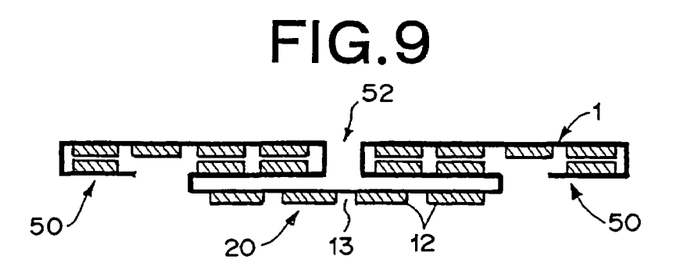
FIG. 9 is an illustrative sectional view of the portion of the multilayer construction of the absorbent easily rendered three-dimensional in the fifth example.

FIG. 9 shows the same side portions of the multilayer construction 50 as in FIG. 8, but the center portion of the multilayer construction 20 is formed to be folded to the reverse surface side at the widthwise center of the absorbent sheet 1, thereby a channel 52 is formed in the center of the center portion of the multilayer construction 20. This channel 52, when fluid is absorbed by the absorbent easily rendered three-dimensional, first retains this fluid in channel 52, and what is retained here will be absorbed and held, as time goes by, by the area with super-absorbent material 12 which surrounds channel 52. Also, the side portions of the multilayer construction will rise upward and serve as leakage prevention walls at the side edges.

In each example explained so far, the construction of the absorbent easily rendered three-dimensional of the present invention has a portion of the multilayer construction formed in the center widthwise, by folding the absorbent sheet. It can also form a portion of the multilayer construction using a number of areas with absorbent material in the central region longitudinally of the main absorbing area of the absorbent easily rendered three-dimensional, extending in a band shape in the longitudinal direction of the absorbent sheet. Some examples of the absorbent easily rendered three-dimensional provided with these portions of the multilayer construction are shown below.

Figure 10A:
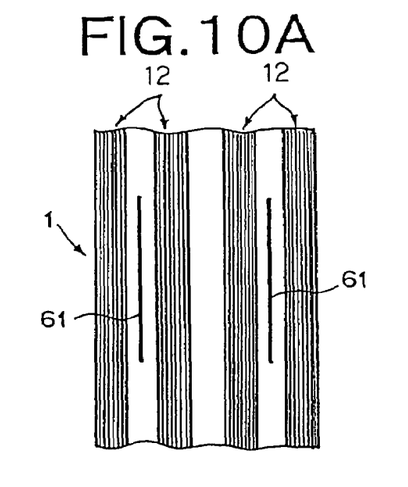
FIGS. 10A and 10B are oblique views of the portion of the multilayer construction of the absorbent easily rendered three-dimensional in the sixth example.
Figure 10B:
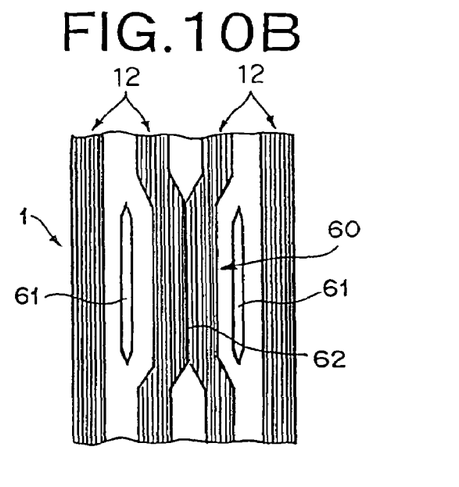

FIG. 10A shows the absorbent sheet 1 with a number of (four in this example) areas with super-absorbent material 12 extending along the folding lines in the longitudinal direction in parallel to one another, and FIG. 10B shows the absorbent easily rendered three-dimensional with a portion of the multilayer construction 60 formed by bringing together and bonding, only at the lengthwise central region of the absorbent sheet 1, the two adjacent areas with super-absorbent material 12 located in the center and contacting each other.

As a means of bringing together and bonding two adjacent areas with super-absorbent material 12, as shown in the mode of this example demonstrated in FIG. 10A, the slit cuts 61 are made at locations within the areas without super-absorbent material on both sides widthwise of the central portion of the multilayer construction to be formed, in the absorbent sheet 1 with a number of (four in this example) areas with super-absorbent material 12 extending in the longitudinal direction in parallel to one another, and the central portion of the multilayer construction 60 is formed, as shown in FIG. 10B, by bringing into contact with each other the areas with super-absorbent material 12 which are sandwiched between the two slit cuts 61, and by bonding them by means of hot melt and the like at the bonding surface 62.

Figure 11A:
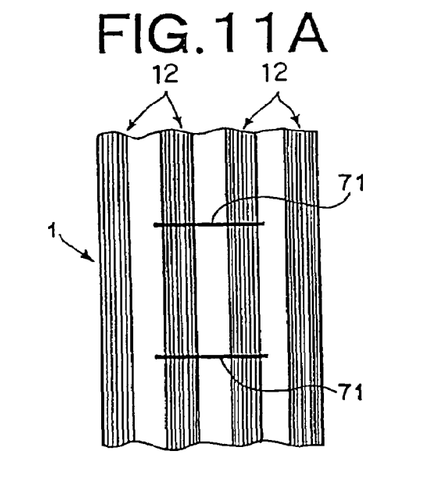
FIGS. 11A and 11B are oblique views of the portion of the multilayer construction of the absorbent easily rendered three-dimensional in the seventh example.
Figure 11B:
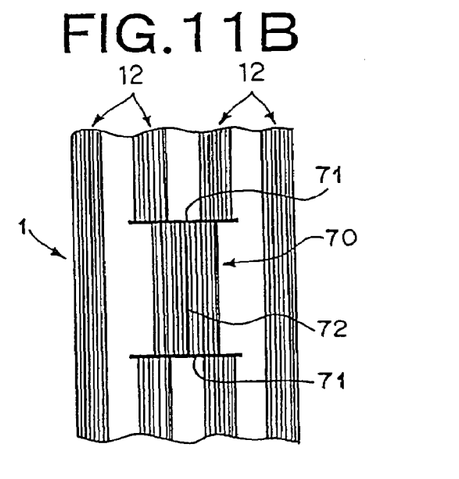

Or, as shown in FIG. 11A, the two spaced slit cuts 71, extending in a direction perpendicular to lengthwise, are made in parallel with each other in the central region lengthwise of the central portion of the multilayer construction to be formed, in the absorbent sheet 1 with a number of (four in this example) areas with super-absorbent material 12 extending in the longitudinal direction in parallel to one another, and the central portion of the multilayer construction 70 may also be formed by bringing into contact with each other the areas with super-absorbent material 12 in the region isolated from the rest by these slit cuts 71 and 71, and by bonding them by means of hot melt and the like at the bonding line 72.

With the presence of slit cuts as described above, in the absorbent easily rendered three-dimensional of this present invention, the said portion of the multilayer construction is made free from a binding effect from adjacent portions, resulting in the benefit of allowing even more readily bulging by absorbing liquid. Furthermore, provision of slit cuts makes it possible for the discharged liquid human waste to physically penetrate and move to the lower layer area, facilitating effective dispersing of liquid between the liquid permeable sheet and the liquid impermeable back sheet disposed in the back surface of the absorbent easily rendered three-dimensional, making possible absorption by both sides of the absorbent easily rendered three-dimensional.

The absorbent easily rendered three-dimensional of this present invention with the above-described construction comprising an absorbent sheet with the areas with super-absorbent material and the areas without super-absorbent material alternately formed in band shape parallel to each other along the longitudinal direction of the substrate sheet has better liquid-absorbing and holding performance when a portion of the multilayer construction in the central region is present, than when it is flat, but in order to respond to the condition in which a further amount of liquid is supplied, concentrated in a short period of time, a layer with a so-called acquisition function that temporarily retains the liquid may be added.

Figure 12:
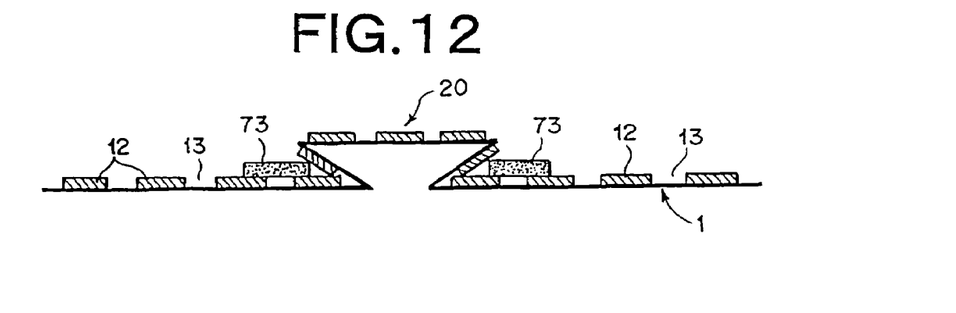
FIG. 12 is a sectional view of the portion of the multilayer construction of the absorbent easily rendered three-dimensional in the eighth example.
Figure 13:
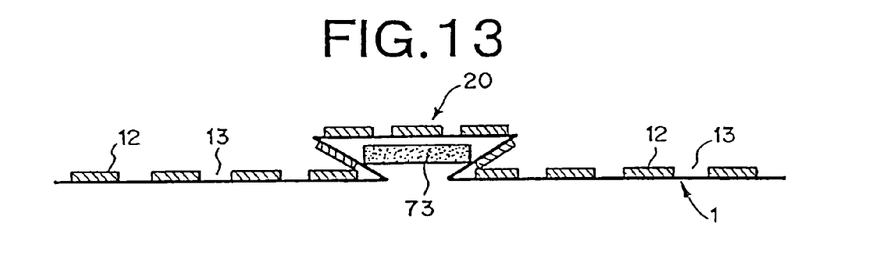
FIG. 13 is a sectional view of the absorbent easily rendered three-dimensional in the ninth example.

FIG. 12 shows the view of the absorbent easily rendered three-dimensional, the same as the one shown in FIG. 1, which has the portion of the multilayer construction 20, and with an acquisition layer 73 provided in the absorbent easily rendered three-dimensional, positioned along both sides of the said portion of the multilayer construction and extending in a longitudinal direction This acquisition layer 73, as shown in FIG. 13, may also be positioned in the space provided within the portion of the multilayer construction 20 by folding in a Ω form.

Figure 14A:
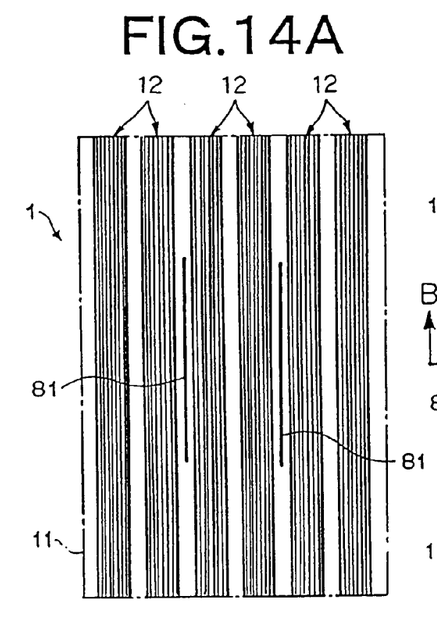
FIGS. 14A, 14B and 14C are plan views and a sectional view of the portion of the multilayer construction of the absorbent easily rendered three-dimensional in the tenth example.
Figure 14B:
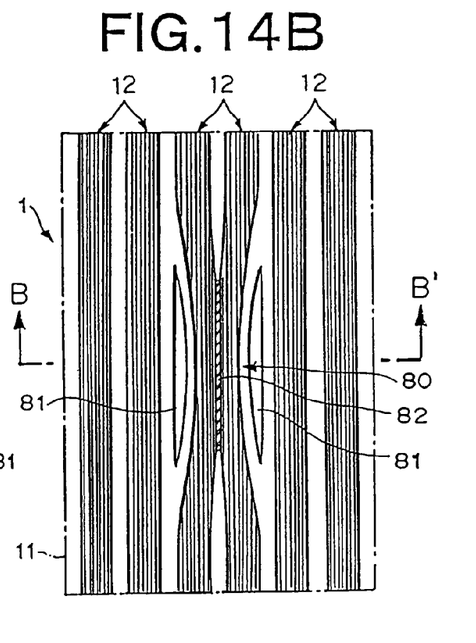
Figure 14C:
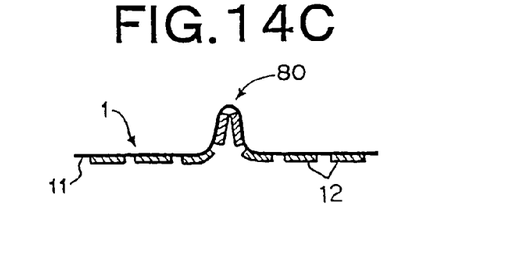
Figures 15A, 15B:
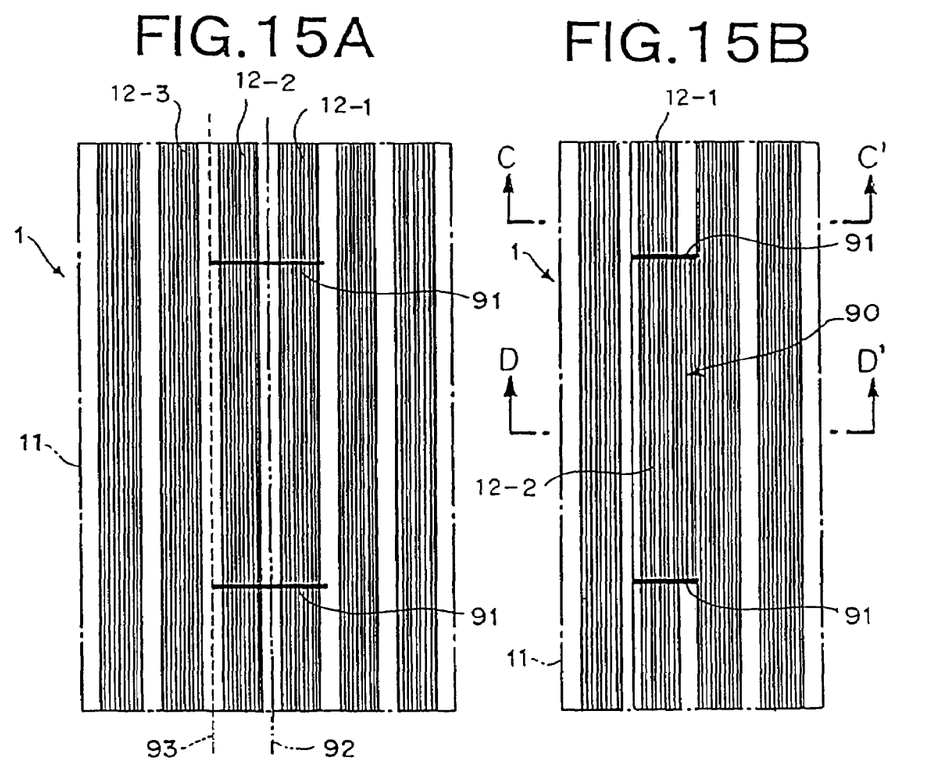
FIGS. 15A, 15B, 15C and 15D are plan views and sectional views of the portion of the multilayer construction of the absorbent easily rendered three-dimensional in the eleventh example.
Figure 15C:
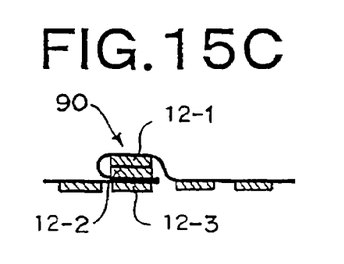
Figure 15D:
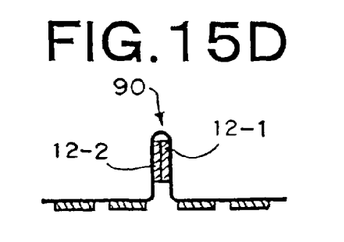
Figure 16A:
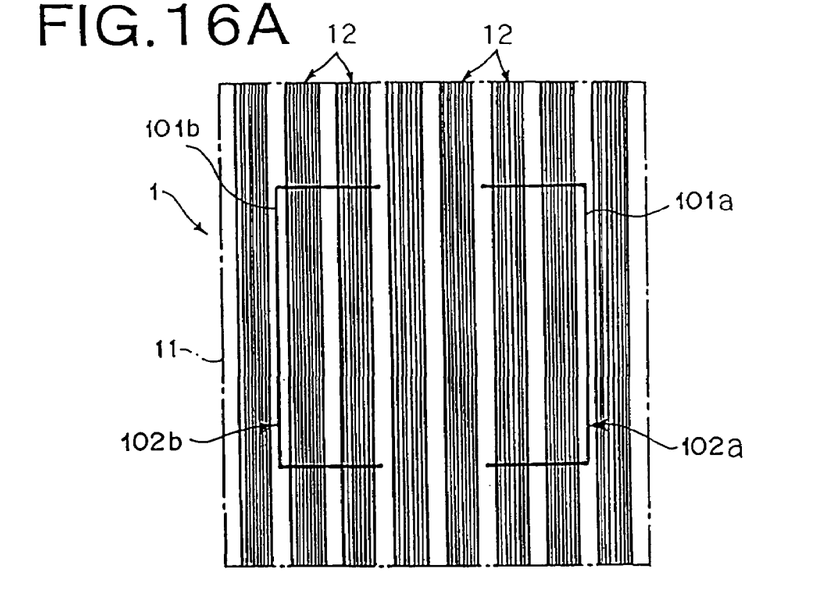
FIGS. 16A, 16B and 16C are plan views and a sectional view of the portion of the multilayer construction of the absorbent easily rendered three-dimensional in the twelfth example.
Figure 16B:
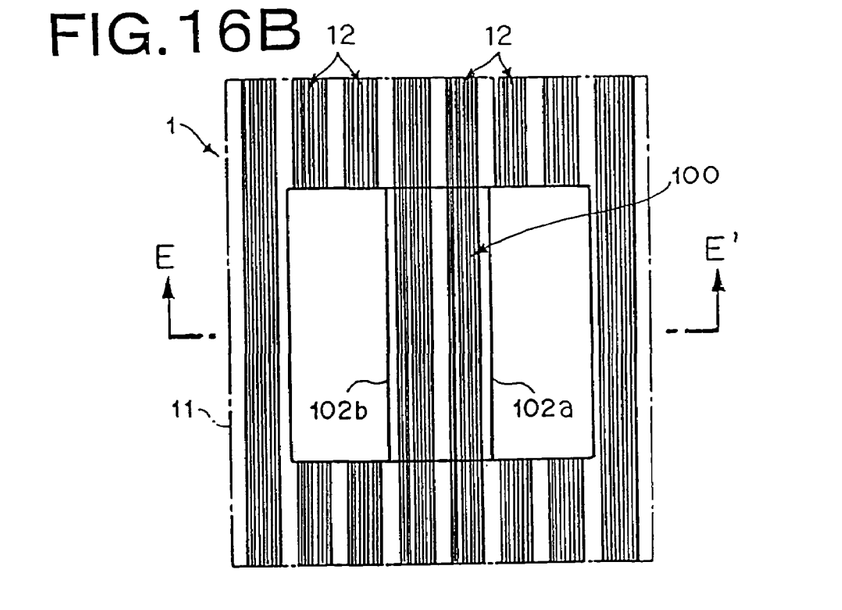
Figure 16C:
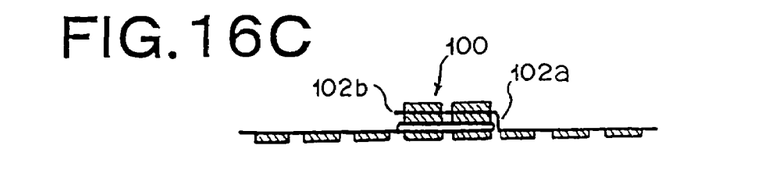

The views in FIG. 14 through FIG. 16 display other examples of folding configurations applicable to the present invention. As shown in FIG. 14A, in the absorbent sheet 1 with a plural number of areas with super-absorbent material 12 in parallel to one another, the slit cuts 81 are made in the substrate sheet 11, or at locations within the areas without super-absorbent material, outside the two central areas with super-absorbent material 12, and as shown in FIGS. 14B and 14C, the undersurfaces of the areas with super-absorbent material 12 which are sandwiched between the two slit cuts 81, are made to contact each other, and by bonding them by means of adhesive 82 and the like the protruding multilayer construction 80 is formed in the central region of the absorbent easily rendered three-dimensional 1.

In the example shown in FIG. 15 of the absorbent sheet 1 with a plural number of areas with super-absorbent material 12, the two spaced slit cuts 91 and 91 are made in the center lengthwise, straddling the two adjacent areas with super-absorbent material 12-1 and 12-2, and then inside the area with super-absorbent material 12-1 (between 12-1 and 12-2) within the area without super-absorbent material between the above slit cuts, a valley fold is made along the folding line 92 extending in the longitudinal direction within the area without super-absorbent material, and then opposite from it, outside the area with super-absorbent material 12-2, a mountain fold along the folding line 93 is made within the areas without super-absorbent material, and then as shown in FIG. 15C, the area with super-absorbent material 12-1 is folded so as to be on top of the adjacent area with super-absorbent material 12-2 making the three-layer lamination structure. Furthermore, as shown in FIG. 15D, the double layer configuration made of the areas with super-absorbent material 12-1 overlapping 12-2 is raised between the two slit cuts, 91 and 91, to form the bulging center portion of the multilayer structure 90.

Furthermore, in the example shown in FIG. 16, of the absorbent sheet 1 with a multiple number of areas with super-absorbent material 12, two spaced slit cuts are made to cut a plural number of adjacent areas with super-absorbent material 12 (two in this example) in two places separated in the longitudinal direction, and then at the end of one slit cut, another slit cut extends in the lengthwise direction to the end of other slit cut, forming the slit cuts 101a arranged in the shape of a Japanese letter ⊐, or ko, and at the same time the resultant flap 102a. Similarly at a location in a given distance widthwise from this flap 102a, the second set of slit cuts 101b is made symmetrically with 101a. These two flaps 102a and 102b are layered by being folded inwardly as shown in FIG. 16B, overlapping the portions between them, and thereby as shown in FIG. 16C, a portion of the multilayer construction 100, or 2 bands of the three layers of areas with super-absorbent material 12 is formed in the center of the absorbent sheet 1.

For the absorbent sheet 1 in this type of construction, it is possible for its center portion of the multilayer construction 100 to bulge high when fluid is absorbed; furthermore, the area adjacent to the center portion of the multilayer construction 100 where flap 102a and 102b used to be has now become openings, making it possible for the discharged fluid waste to physically penetrate and move to the lower layer through these openings, making retention, dispersion, and absorption of discharged liquid waste in the lower layer readily possible.

The absorbent easily rendered three-dimensional, of the present invention, that has various forms of multilayer construction as described above, can be incorporated as an absorbent sheet in various absorptive products, and displays excellent absorbing performance, as detailed above.

Figure 17:
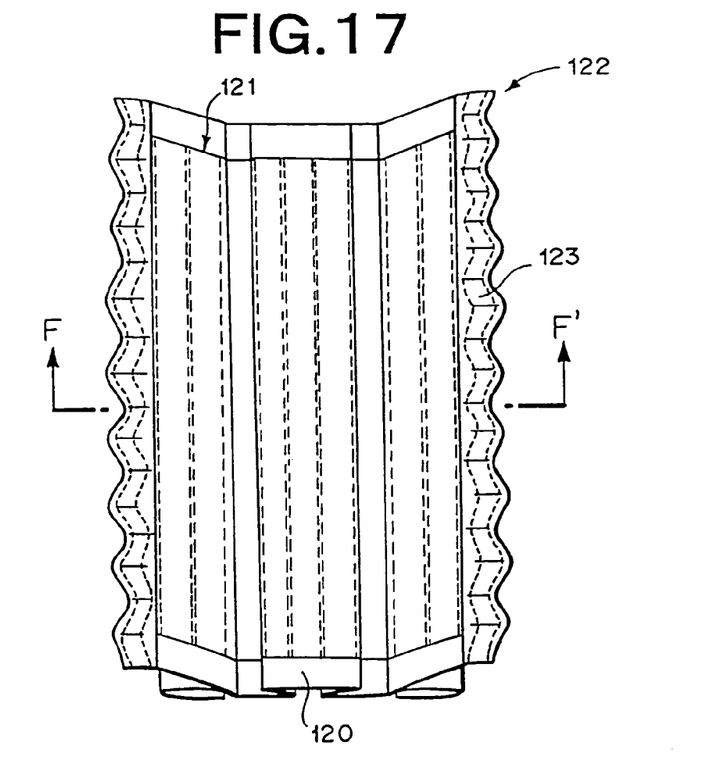
FIG. 17 is an oblique view showing an absorptive product comprising the absorbent easily rendered three-dimensional of the present invention.
Figure 18:
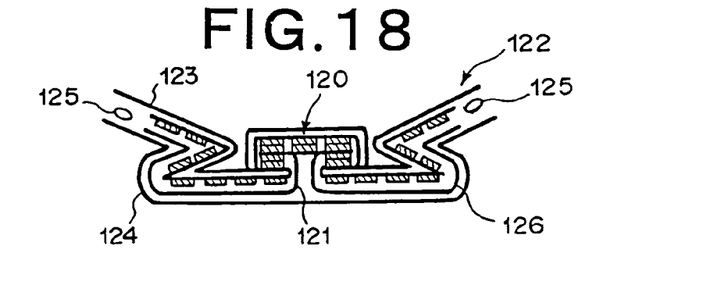
FIG. 18 is a sectional view of FIG. 17 taken along line F-F'.

FIG. 17 and FIG. 18 show one example of an absorptive product 122 composed of the absorbent easily rendered three-dimensional 121 which formed the center portion of the multilayer construction 120. In FIG. 17 and FIG. 18, code 123 corresponds to the top sheet, 124 the back sheet, 125 the elastic member, and 126 corresponds to tissue respectively. An absorptive product 122 in this kind of construction, as liquid is supplied, due to the great absorbing capacity of the center portion of the multilayer construction 120, carries out effective absorption, and at the same time, this center portion of the multilayer construction 120 bulges, providing a fit to the convex and concave contour of the human body, and displaying excellent leakage preventing capability.

Figure 19:
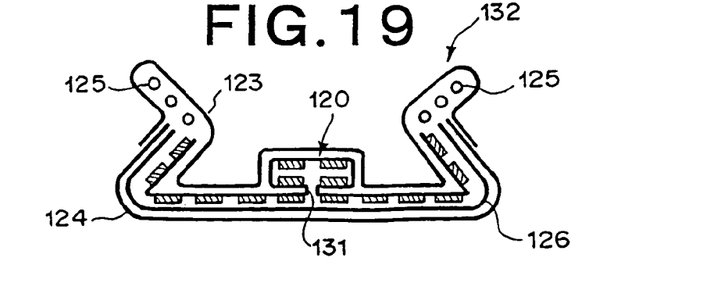
FIG. 19 is a sectional view of another absorptive product comprising the absorbent easily rendered three-dimensional of the present invention.

FIG. 19 shows another mode of absorptive product 132 made using the similar absorbent easily rendered three-dimensional 131.

As explained above, the absorptive products of the present invention are composed of the liquid permeable top sheet, the liquid impermeable back sheet, and the main body of absorbent disposed between these sheets, having a folded configuration in the center widthwise, it absorbs and holds the body fluid. The said folded configuration may be formed by laminating the top sheet and back sheet after folding the absorbent body, or reversely it may be folded after laminating the absorbent body and back sheet first.

INDUSTRIAL APPLICATION

As explained above, because the absorbent easily rendered three-dimensional of the present invention has, in the central region widthwise, a multilayer construction of at least two layers of absorbent sheets comprising the absorbent easily rendered three-dimensional, when the liquid supplied is absorbed, this port ion of the multilayer construction quickly absorbs the liquid, spontaneously becomes three-dimensional by bulging higher than the other portions, closely fits the wearer's body, and effectively prevents leakage of liquid. The absorbent easily rendered three-dimensional of the present invention, therefore, is suitable for absorption products intended to be used for absorbing and holding discharged human liquid waste.

The invention claimed is:

1. An absorbent whose central area is easily rendered three-dimensional by bulging by water absorption characterized in that, where the absorbent is comprised of an absorbent sheet, wherein said absorbent sheet comprises a substrate sheet and super-absorbent materials coated on said substrate sheet whereby a plurality of band-shaped areas with super-absorbent materials and a plurality of continuous band-shaped areas without super-absorbent materials are formed on said substrate sheet, with these band-shaped areas extending alternately in parallel lines, lengthwise on said substrate sheet, at least one band-shaped portion of multilayer construction is formed by said absorbent sheet being folded in said area without super-absorbent materials located in the widthwise center along a folding line in said area without super-absorbent materials of said absorbent sheet, then being folded again this time in the opposite direction in said area without super-absorbent materials which is located at a desired distance from the above folded position, forming a valley fold so that each folded portion faces the other, wherein said areas with super-absorbent materials are superposed in at least three layers in some parts.

2. The absorbent whose central area is easily rendered three-dimensional by bulging by water absorption, according to claim 1, wherein said portion of multilayer construction is present throughout the length of the absorbent sheet.

3. The absorbent whose central area is easily rendered three-dimensional by bulging by water absorption, according to claim 1, wherein said portion of multilayer construction has a length one half or less than one half of the entire length of the absorbent sheet and is present only in the center region in the longitudinal direction of the absorbent sheet.

4. The absorbent whose central area is easily rendered thee-dimensional by bulging by water absorption, according to claim 1, wherein slits are formed to extend in a longitudinal direction of the absorbent sheet in the areas without super-absorbent materials positioned on both sides, across the width, of said portion of multilayer construction, thus allowing the bulging, by absorbing liquid, of said portion of multilayer construction, and with no widthwise binding effect from other portions.

5. The absorbent whose central area is easily rendered three-dimensional by bulging by water absorption, according to claim 1, wherein a central zone is formed with two spaced slits extending in the direction perpendicular to the longitudinal direction of the absorbent sheet in the center region of said portion of multilayer construction, thus allowing the easy bulging, by absorbing liquid, of the central zone of said portion of multilayer construction, with no lengthwise binding effect from other portions.

6. The absorbent whose central area is easily rendered three-dimensional by bulging by water absorption, according to claim 1, wherein the distance between said valley folds opposite each other is retained at 5 mm or more, and said portion of the multilayer construction bulges with two peaks when liquid is absorbed.

7. The absorbent whose central area is easily rendered three-dimensional by bulging by water absorption, according to claim 1, wherein the side portions of the multilayer construction formed by folding said absorbent sheet are on both sides of said portion of the multilayer construction formed in the center region widthwise of said absorbent sheet with an appropriate space in between, and troughs to channel fluid are formed between said center portion of the multilayer construction and each side portion of the multilayer construction.

8. The absorbent whose central area is easily rendered three-dimensional by bulging by water absorption, according to claim 7, wherein band-shaped acquisition layers extending along both sides of said side portions of the multilayer construction are further provided.

9. The absorbent whose central area is easily rendered three-dimensional by bulging by water absorption, according to claim 1, wherein band-shaped acquisition layers are further provided to extend longitudinally along an undersurface of at least one portion of the multilayer construction of said center portion and each side portion of the multilayer construction.

10. The absorbent whose central area is easily rendered three-dimensional by bulging by water absorption, according to claim 1, wherein said areas with super-absorbent materials formed on said absorbent sheet are composed of a super absorbent layer with a super-absorptive resin content ratio of 50% or more and said areas without super-absorbent materials are made of said substrate sheet only.

11. The absorbent whose central area is easily rendered three-dimensional by bulging by water absorption, according to claim 1, wherein the areas with super-absorbent material and the areas without super-absorbent material of said absorbent sheet are distributed alternately in continuous narrow lines.

12. An absorptive product, comprising the absorbent according to claim 1, wherein the absorptive product is easily rendered three-dimensional in a portion having the absorbent by water absorption.

* * * * *